United States Patent [19]

Kunz

[11] 4,384,879
[45] May 24, 1983

[54] 4-(1H-AZOLYLMETHYL)-1,3-DIOXOLAN-5-ONE DERIVATIVES, PRODUCTION THEREOF AND USE THEREOF AS GROWTH REGULATORS AND/OR MICROBICIDES

[75] Inventor: Walter Kunz, Oberwil, Switzerland

[73] Assignee: Ciba-Geigy Corporation, Ardsley, N.Y.

[21] Appl. No.: 280,387

[22] Filed: Jul. 6, 1981

[30] Foreign Application Priority Data

Jul. 15, 1980 [CH] Switzerland .......................... 5412/80

[51] Int. Cl.³ ..................... A01N 43/50; A01N 43/64; C07D 405/06
[52] U.S. Cl. .......................................... 71/76; 71/78; 71/92; 424/232; 424/245; 424/269; 424/273 R; 424/279; 548/336; 548/101; 548/262; 549/265; 549/296; 562/470
[58] Field of Search ...................... 548/101, 262, 336; 424/245, 232, 269, 273 R; 71/76, 78, 92

[56] References Cited

U.S. PATENT DOCUMENTS 4,351,839  9/1982  Chan ................................... 548/262

FOREIGN PATENT DOCUMENTS 44276  1/1982  European Pat. Off. .

OTHER PUBLICATIONS

Palomaa, Salmi & Wallin, "Studien über ätherartige Verbindungen, XV, Mitteil", Chem. Ber. 68, 609–618, (1935).
Salmi & Pohjolainen, "Untersuchurgen über ätherartige Verbindungen, IV, Mitteil", Chem. Ber. 72, 798–803, (1939).
Smith & Burnett, "Effectiveness of Repellents Applied to Clothing for Protection Against Salt–Marsh Mosquitoes", Chemical Abstracts 44, 6567a, (1949).
Organic Syntheses 3, 326, 526, 538, (1955).
Compere, "Synthesis of α-Hydroxyarylacetic Acids from Bromoform, Arylaldehydes, and Potassium Hydroxide . . . ", J. Org. Chem. 33, 2565–2566, (1968).
Farines & Soulier, "Etude de Dioxolanones–4: Syntheses et Proprietes Physiques", Bull. Soc. Chim. 1970, 332–340.

Primary Examiner—Alton D. Rollins
Attorney, Agent, or Firm—Frederick H. Rabin

[57] ABSTRACT

The invention relates to novel 4-(1H-azolylmethyl)-1,3-dioxolan-5-one derivatives of the formula I

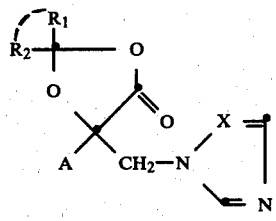

and to the production and use of these compounds. In formula I, $R_1$ and $R_2$ are unsubstituted or substituted alkyl or phenyl, or together form a 3- to 7-membered carbocyclic ring which is unsubstituted or substituted, A is an unsubstituted or substituted phenyl radical, and X is —CH= or —N=. The compounds of the formula I can be used in the form of appropriate compositions for regulating plant growth and/or for controlling and/or protecting plants from attack by phytopathogenic microorganisms.

16 Claims, No Drawings

4-(1H-AZOLYLMETHYL)-1,3-DIOXOLAN-5-ONE DERIVATIVES, PRODUCTION THEREOF AND USE THEREOF AS GROWTH REGULATORS AND/OR MICROBICIDES

The present invention relates to substituted 4-(1H-azolylmethyl)-1,3-dioxolan-5-one derivatives of the formula I and acid addition salts thereof with organic and inorganic acids, and the metal complex salts thereof. The invention also relates to the production of these compounds and to growth regulating and/or microbicidal compositions which contain one of the compounds of formula I as active ingredient. The invention also relates to the use of compounds of the formula I for regulating plant growth and/or controlling harmful microorganisms.

The invention comprises compounds of the formula I

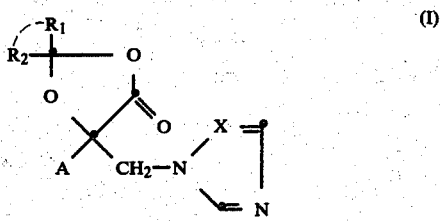

wherein each of $R_1$ and $R_2$ independently is hydrogen, $C_1$–$C_8$alkyl unsubstituted or mono- or polysubstituted by halogen, $C_1$–$C_4$alkoxy, $C_1$–$C_4$alkylthio, phenyl or phenoxy, or is phenyl, all of which phenyl radicals are unsubstituted or mono- or polysubstituted by halogen, nitro, trifluoromethyl, $C_1$–$C_4$alkyl or methoxy, or $R_1$ and $R_2$ together form a 3- or 7-membered carbocyclic ring which is unsubstituted or substituted by halogen, $C_1$–$C_4$alkyl, $C_1$–$C_4$alkoxy or $C_1$–$C_3$alkylthio. A is a phenyl radical unsubstituted or mono- or polysubstituted by halogen, trifluoromethyl, nitro, $C_1$–$C_4$alkyl, $C_1$–$C_4$alkoxy or phenyl, and X is —CH= or —N=, together with the acid addition salts thereof with organic or inorganic acids, and also the metal complex salts thereof.

Accordingly, the compounds of the formula I comprise the free compounds, their acid addition salts and their metal complexes.

Depending on the indicated number of carbon atoms, alkyl by itself or as moiety of another substituent denotes e.g. the following groups: methyl, ethyl, propyl, butyl, pentyl, hexyl, heptyl or octyl, as well as the isomers thereof, e.g. isopropyl, isobutyl, tert-butyl, isopentyl etc. A 3- to 7-membered carbocyclic ring comprises e.g. cyclopropyl, cyclobutyl, cyclopentyl, cyclohexyl or cycloheptyl. Halogen generally denotes fluorine, chlorine, bromine or iodine, with chlorine or bromine being preferred.

Examples of salt-forming acids are inorganic acids, e.g. hydrohalic acids such as hydrofluoric acid, hydrochloric acid, hydrobromic acid or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals can exist in different valency states. The metal complexes of the formula I can be mononuclear or polynuclear, i.e. they can contain one or more parts of the organic molecule as ligands.

The compounds of the formula I are biologically active substances which can be used both for influencing plant growth and for controlling harmful, in particular phytopathogenic, microorganisms. The compounds of the formula I thus afford the possibility of selectively regulating plant growth and simultaneously of protecting plants from pathogens. The 1,2,4-triazolyl derivatives within the scope of formula I are preferred.

On account of their pronounced growth regulating and/or microbicidal action, preferred compounds of the formula I are those which contain the following types of substituents or combinations thereof.

For $R_1$ and $R_2$ independently of each other:

(a) hydrogen, $C_1$–$C_8$alkyl, phenyl which is unsubstituted or substituted by halogen, nitro, trifluoromethyl, methyl or ethyl, or benzyl; or in particular (b) hydrogen, $C_1$–$C_5$alkyl, phenyl; in particular (c) $C_1$–$C_5$alkyl.

For A:

(a) phenyl, unsubstituted or mono- or polysubstituted by halogen, trifluoromethyl, nitro, $C_1$–$C_4$alkyl, $C_1$–$C_4$alkoxy or phenyl; or in particular:

(b) phenyl, unsubstituted or mono- or polysubstituted by halogen, $C_1$–$C_3$alkyl, methoxy or phenyl; in particular (c) phenyl, 2,4-dichlorophenyl, 2,4-dibromophenyl, 2-chloro-4-fluorophenyl, 4-chlorophenyl, 4-bromophenyl.

For X: —CH= or, in particular, —N=.

A preferred group of growth regulating and/or microbicidal compounds comprises those of the formula I, wherein each of $R_1$ and $R_2$ independently is hydrogen, $C_1$–$C_8$alkyl, phenyl which is unsubstituted or substituted by halogen, nitro, trifluoromethyl, methyl or ethyl, or is benzyl; A is phenyl, unsubstituted or mono- or polysubstituted by halogen, trifluoromethyl, nitro, $C_1$–$C_4$alkyl, $C_1$–$C_4$alkoxy or phenyl; and X is —CH= or —N=.

A further preferred group of growth regulating and/or microbicidal compounds comprises those of the formula I, wherein each of $R_1$ and $R_2$ independently is hydrogen, $C_1$–$C_5$alkyl or phenyl; A is phenyl, unsubstituted or mono- or polysubstituted by halogen, $C_1$–$C_3$alkyl, methoxy or phenyl; and X is —CH= or —N=.

A particularly preferred group of growth regulating and/or microbicidal compounds comprises those of the formula I, wherein each of $R_1$ and $R_2$ independently is $C_1$–$C_5$alkyl, A is phenyl, 2,4-dichlorophenyl, 2,4-dibromophenyl, 2-chloro-4-fluorophenyl, 4-chlorophenyl or 4-bromophenyl, and X is —CH= or —N=.

Further preferred compounds of the formula I are those wherein $R_1$ and $R_2$ together form a 3- to 7-membered carbocyclic ring which is unsubstituted or substituted by methoxy.

The following individual compounds are especially preferred on account of their pronounced growth regulating and/or microbicidal action:

4-(1H-1,2,4-triazolylmethyl)-4-(4-chlorophenyl)-2,2-dimethyl-1,3-dioxolan-5-one, 4-(1H-1,2,4-triazolylmethyl)-4-(4-bromophenyl)-2,2-dimethyl-1,3-dioxolan-5-one, 4-(1H-1,2,4-triazolylmethyl)-4-(phenyl)-2,2-dimethyl-1,3-dioxolan-5-one, 4-(1H-1,2,4-triazolylmethyl)-4-(2,4-dichlorophenyl)-2,2-dimethyl-1,3-dioxolan-5-one, 4-(1H-imidazolylmethyl)-4-(4-chlorophenyl)-2,2-dimethyl-1,3-dioxolan-5-one, 4-(1H-1,2,4-triazolylmethyl)-4-(4-chlorophenyl)-2,2-diethyl-1,3-dioxolan-5-one, and 4-(1H-1,2,4-triazolylmethyl)-5-(2-chloro-4-fluorophenyl)-2,2-dimethyl-1,3-dioxolan-5-one.

The compounds of the formula I can be obtained by a method as described e.g. hereinbelow.

In the formulae II to VI above, $R_1$ and $R_2$, A and X are as defined for formula I, M is hydrogen or a metal ion, preferably the cation of an alkali metal or alkaline earth metal, and G is one of the customary leaving groups, e.g. alkoxy, benzenesulfonyloxy, p-bromobenzenesulfonyloxy, p-tosyloxy, trifluoroacetyloxy, lower alkylsulfonyloxy such as mesyloxy or, in particular, halogen such as fluorine, chlorine, bromine or iodine, with chlorine or bromine being preferred.

The process for obtaining compounds of the formula I can be carried out e.g. by means of the partial reactions A, B, C, D or E illustrated below:

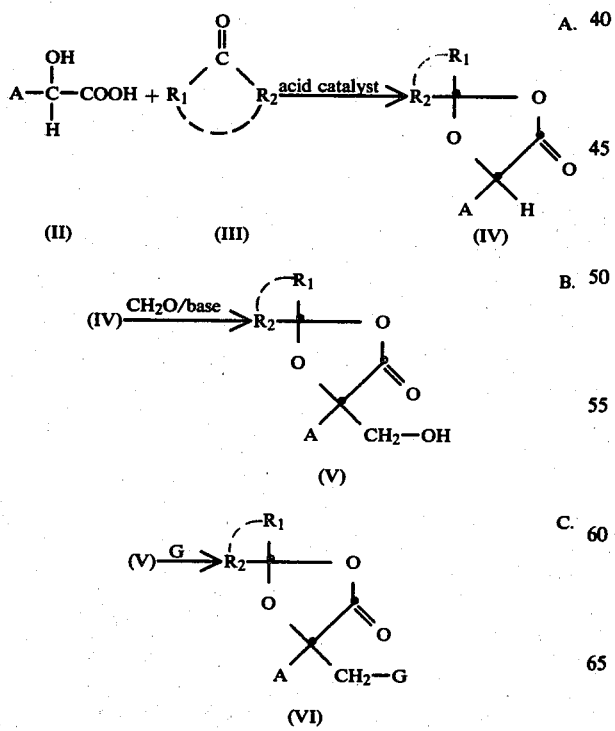

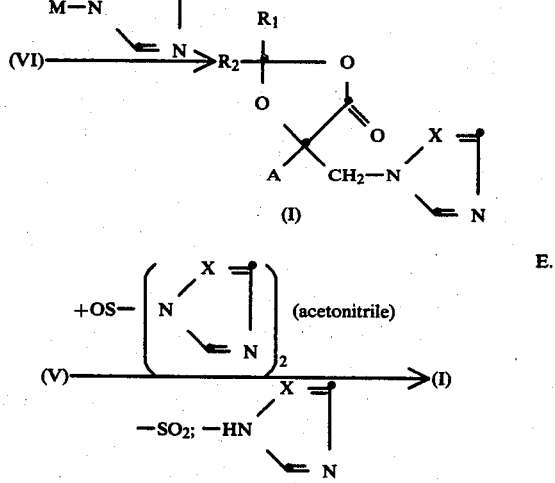

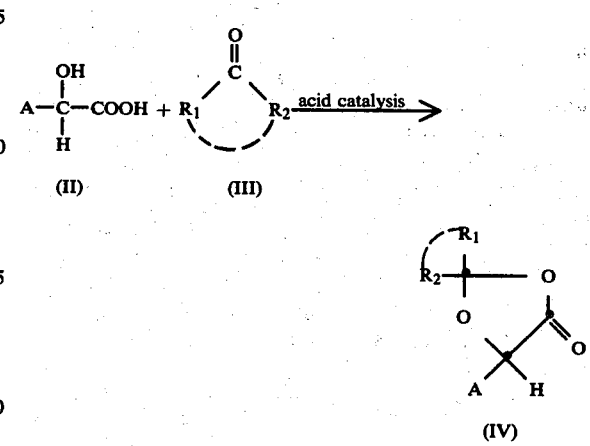

an acid II (which can either be in the form of a racemate or in its pure D- or L-form) is reacted with an open-chain or cyclic ketone or with an aldehyde of the formula (III) to give the dioxolane IV. For this reaction it is possible, in principle, to use solvents which are inert to the reactants and advantageously form azeotropes with water. Examples of suitable solvents are aromatic hydrocarbons such as benzene, toluene, xylenes or halogenated hydrocarbons such as dichloromethane, chloroform, carbon tetrachloride, 1,2-dichloroethane, tetrachloroethylene, chlorobenzene, and also ethereal compounds such as tert-butylmethyl ether, dioxane etc. In some cases the compound of the formula III itself can be used as solvent. The reaction temperature depends largely on the choice of ketone or aldehyde III and be e.g. from −30° to 180° C., preferably from −10° to 140° C. In some cases it is convenient to effect acid catalysis. Examples of suitable catalysts and condensation agents are mineral acids such as hydrohalic acids, sulfuric acid, phosphoric acid, sulfonic acids such as p-toluenesulfonic acid, acid ion exchange resins etc. The water formed can be removed from the reaction mixture not only as an azeotrope but also with the aid of ion exchange resins, molecular resins, or by reaction with dicyclohexylcarbodiimide. It is sometimes advantageous to carry out the reaction under elevated pressure.

In partial reaction B

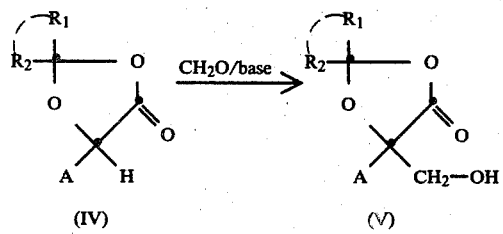

the dioxolanone IV reacts with formaldehyde, advantageously in the presence of a base, to give the intermediate of the formula V. Suitable bases for this reaction are tertiary amines such as trialkylamines, pyridine, dimethylaniline etc., or quaternary ammonium hydroxides such as tetramethylammonium hydroxide. It is possible to use e.g. an equimolar amount of base, based on the product IV. Partial reaction B can be carried out e.g. in the temperature range from $-30°$ to $+80°$ C., using a solvent which is inert to the reactants, e.g. an ethereal compound such as tetrahydrofurane, dioxane etc., or a nitrile such as acetonitrile, propionitrile etc.

In partial reaction C

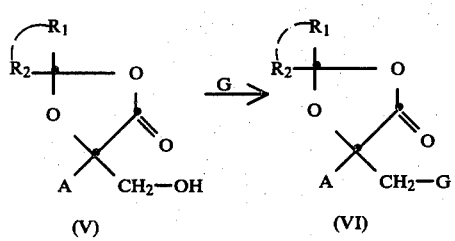

a leaving group G (G can be e.g. one of the customary leaving groups, for example acyloxy, arylsulfonyloxy such as benzenesulfonyloxy, p-bromobenzenesulfonyloxy, p-tosyloxy or alkylsulfonyloxy, especially lower alkylsulfonyloxy such as mesyloxy, or halogen such as fluorine, chlorine, bromine, iodine, preferably chlorine or bromine) is introduced into the molecule V by reacting the intermediate V e.g. with methanesulfonyl chloride, advantageously in the presence of a tertiary amine such as pyridine, trialkylamine, collidine etc., to give the intermediate VI. The amine is employed in at least the molar amount, based on the compound of the formula V. The conventional organic halogenated and non-halogenated aliphatic and aromatic solvents can be employed in this reaction. The leaving group G can either replace the proton or the OH group altogether.

Some of the intermediates of the formula VI have fungicidal activity, e.g. the compounds of the formula VI, wherein A is 2,4-dichlorophenyl and $R_1$ and $R_2$ are alkyl, e.g. methyl.

In partial reaction D

the leaving group G (e.g. $CH_3SO_3-$) is replaced by the substituent $$-N\underset{N}{\overset{X}{\diagup\!\!\!\diagdown}}$$

by converting e.g. the product VI with a compound $$M-N\underset{N}{\overset{X}{\diagup\!\!\!\diagdown}}$$

into the final product of the formula I. The reaction can be conducted in conventional inert organic solvents and in some cases it is convenient to add a base such as an alkali metal or alkaline earth metal carbonate, an alkali alcoholate or sodium hydride.

In partial reaction E

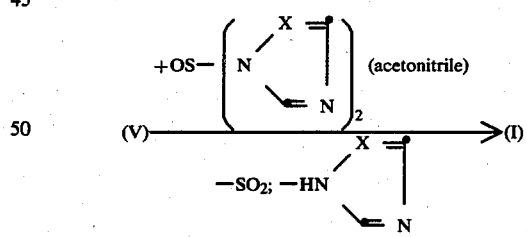

an alcohol of the formula V reacts either with N,N'-thiocarbonyldi-1,2,4-triazole or N,N'-thiocarbonyldiimidazole accompanied by the elimination of $SO_2$ and the corresponding heterocycle to give a final product of the formula I. It can be advantageous to conduct the reaction in a polar organic solvent, e.g. an ether or etheral compound such as diethyl ether, diisopropyl ether, tert-butylmethyl ether, dimethoxyethane, dioxane, tetrahydrofurane, anisole; a nitrile such as acetonitrile or propiononitrile; an ester such as ethyl acetate or butyl acetate; or a dialkylamide such as dimethyl amide. Mixtures of such solvents with one another can also be employed. The reaction can be carried out from temperatures of 20° C. upwards. To hasten the reaction, however, it is advantageous to use higher temperatures, for example from 45° to 90° C. or the boiling point of the solvent or mixture of solvents.

The above preparatory methods also constitute an object of the invention.

The starting compounds of the formulae II and III are known and are obtained by methods which are generally known.

Dioxolanones of the formula IV are mentioned in the following publications: Org.Synth. Coll. Vol. 3, 536 (1955), Bull. Soc. Chim. France 1970, 332, Ber. 68, 303, 609 (1935), Ber. 72, 319, 798 (1939).

Dioxolanones of the formulae V and VI are novel. They have been specially developed for obtaining the compounds of the formula I and are, in addition, valuable intermediates for synthesing agrochemicals. Some also are biologically active and have, in particular, phytofungicidal activity. The compounds of the formulae V and VI therefore also constitute an object of the invention.

The production of α-hydroxycarboxylic acids of the formula II is described in the following publications: J. Org. Chim. 33, 2565 (1968), Org. Synth. Coll. Vol. 3, 326 (1955), and Org. Synth. Coll. Vol. 3, 538 (1955). 2-Methyl-2-ethyl-4-phenyl-1,3-dioxolan-5-one is known from J. Econ. Entomol. 42, 439 (1949) and 2,2-dimethyl-4-phenyl-1,3-dioxolan-5-one is known from U.S. patent application 70 388 [CA 46, 3209d (1952)]. Insecticidal activity only is reported for both compounds.

The compounds of formula I contain, vicinal to the substituent A, an asymmetrical carbon atom *C and a further centre of asymmetry (*), if $R_1$ and $R_2$ are different. The latter is adjacent to the two oxygen atoms.

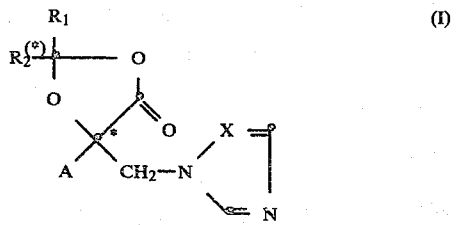

(a) If $R_1$ and $R_2$ are identical, both stereoisomers can be separated by conventional methods, e.g. fractional crystallisation of the salts of compounds of the formula I with an optically active acid such as camphorsulfonic acid, into the optical antipodes. However, the same objective can also be achieved by a selective synthesis of the enantiomers, starting from an optically pure hydroxycarboxylic acid II (partial reaction A).

(b) If $R_1$ and $R_2$ are different, then 4 stereoisomers are obtained. If desired, separation of the pairs of diastereomers (cis-trans isomers) into the racemates can also be efffcted by conventional methods, e.g., by column chromatography. A further separation of the pure diastereomers (cis-trans isomers) into the optically pure enantiomers can be carried out by the separation method described in (a).

The individual configurations can be characterised spectroscopically, e.g. by NMR spectroscopy or X-ray structural analysis. The present invention relates to all isomers, their salts and metal complexes.

Surprisingly, it has now been found that the novel compounds of the formula I and compositions containing them are characterised in particular by their selective influence on plant metabolism. This selective influence on the physiological processes of plant development makes it possible to use the compounds of formula I for different purposes, especially for those in connection with increasing the yield of useful plants, with faciliating harvesting, and with labour-saving in measures taken in crops of cultivated plants.

The compounds of the formula I disclosed herein can be used for regulating the growth of plants. Previous experience with the application of growth regulators has shown that the active ingredients can act on the plants in one or more different ways. These different actions depend largely on the time of application, i.e. on the development stage of the seed or plant, on the nature of the application, and, in particular, on the concentrations employed. Such actions, however, differ in turn from one type of plant to another. Accordingly, the application of compounds of the formula I affords the possibility of influencing the growth of plants in the manner desired.

The novel compounds of the formula I and compositions containing them inhibit the vegetative growth of plants and are thereby able to increase the crop yield substantially. For example, the vegetative growth of soybean plants and other leguminosae such as beans, peas or lentils is reduced and the generative growth promoted, resulting in a direct increase in crop yield. The vegetative growth of other varieties of plants, e.g. vines, cereals, grasses and ornamentals, is inhibited in desired manner. In addition, a marked strengthening of the supporting tissue of the treated plants is observed.

An important kind of plant regulation resides in the special property of compounds of the formula I, when used in rates of application of 0.2 to 5 kg a.i./ha, of effecting in specific plants, especially in cereal cops, a selective growth inhibition which substantially increases the breaking strength of the plants while the crop yield remains unchanged. This results in an economically very interesting method of protecting crops against lodging caused by storms or adverse weather conditions. Moreover, a selective inhibition of the vegetative growth of many cultivated plants permits more plants to be grown per unit of area, which results in a pronounced crop yield with the same fruit setting and the same crop area. The use of growth inhibitors also results in a more effective utilisation of nutrients, which then increasingly benefit the flower formation and fructification. In this manner it is possible to achieve higher crop yields with a simultaneous reduction in the amount of plant residues (e.g. straw, potato haulm, beet leaves).

Particular attention is also drawn to the possibility of inhibiting the undesired growth of suckers in different species of plants, especially in tobacco plants, with the compounds and compositions of the invention, when the leading shoot has been cut off shortly before flowering in order to bring about the desired increase in growth of the leaves.

In contrast to the effects described hitherto obtained with the compounds of the invention at low concentrations, a higher rate of application, e.g. 5 to 10 kg a.i./ha, results in a very pronounced growth reduction—or even in dwarfism—in a number of monocots and dicots. From the standpoint of maintaining arable land, this effect provides a particularly advantageous method of inhibiting harmful plants to the extent that, independently of the growth of useful plants, a uniform low plant cover is retained, which counteracts soil erosion by wind or water. This field of use includes in particular the reduction in growth of grasses in connection with the maintenance of pure grass cultivations such as those established in public parks and open spaces, in urban areas, industrial sites or along trunk roads, on railway embankments or on the embankments of water bodies. In all these cases it is usually necessary to cut the turf or grass periodically. This operation is not only very time-consuming, complicated and expensive in respect of labour and machinery, but also involves the personnel concerned and road users in considerable hazard in the traffic sector.

For this reason there is an urgent need in areas with extensive traffic networks, on the one hand to maintain and cultivate the grassy covering necessary for strengthening road shoulders and embankments on traffic routes and, on the other, to keep it at average height by simple means during the entire vegetation period. This need is fulfilled in a very advantageous manner by applying the compounds of the formula I.

In addition to the growth inhibiting properties, the compounds of the formula I are also able in some cases to influence plant metabolism. In this manner the use of growth inhibitors is able to bring about an improvement in the quality of crop products. In addition to increasing the size and weight, it is possible to increase e.g. the protein content of leguminosae such as beans, lentils, peas and, in particular, of soybeans.

Further, the compounds of the formula I favourably influence germination capacity, flower formation and fruit development. Application of the compounds of the invention does not bring about any change in the life cycle of the plant which is determined by genetic characteristics, i.e. it does not cause mutation.

Surprisingly, it has also been observed that the compounds of the formula I and compositions containing them have, for practical purposes, a very advantageous microbicidal spectrum in addition to their advantageous growth regulating properties. Accordingly, a further field of use of compounds of the formula I is the control of harmful microorganisms, especially of phytopathogenic fungi. Accordingly, these compounds have a very useful curative and preventive action for protecting cultivated plants without adversely affecting these by undesirable side-effects. Examples of cultivated plants within the scope of this invention are: cereals (wheat, barley, rye, oats, rice), beet (sugar beet and fodder beet), dropes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), or plants such as maize, tobacco, nuts, coffee, sugar cane, tea, vines, hops, bananas and natural rubber plants. Within the scope of this invention, plants are also all kinds of greenery, whether ornamentals, areas of grass, embankments or low soil covers in general which counteract erosion or drying out of the soil, and the soil covers desired in cultivations of trees and perennials (fruit plantations, hop plantations, maize fields, vineyards etc.).

With the compounds of formula I it is possible to inhibit or destroy the microorganisms which occur in plants or parts of plants (fruit, blossoms, leaves, stems, tubers, roots) in these or related crops of useful plants, and also to protect from attack by such microorganisms the parts of plants that grow later.

The compounds of the formula I effective, inter alia, against the phytopathogenic fungi which belong to the following classes:against the Oomycetes belonging to the class of the Phycomycetes (e.g. Phytophthora); against fungi imperfecti, e.g. Cercospora; and especially against the Erysiphe and Venturia pathogens belonging to the class of the Ascomycetes, as well as against Basidiomycetes, in particular rust fungi such as Puccinia.

In addition the compounds of formula I have a systemic action. They can also be used as seed dressing agents for protecting seeds (fruit, tubers, grains) and plant cuttings from fungus infections and from phytopathogenic fungi which occur in the soil.

By far the greatest advantage in the practical use of compounds of the formula I in the field of agriculture consists in the fact that two important problems, namely on the hand the strengthening of the plant in the form of a morphological stabilisation and, on the other, the protection of the plant against diseases, are solved simultaneously, in simple manner, by the application of a single compound or composition in the concentration range from 0.05 to 5 kg a.i./ha, preferably from 0.2 to 5 kg a.i./ha. The use of the compounds of the invention accordingly substantially reduces the impact on the environment. In addition, there is the direct effect, observed in most cases, of a marked increase in the crop yield of cultivated plants.

The invention thus relates to the use of the compounds of the formula I for regulating plant growth and/or for controlling and/or preventing attack by microorganisms.

The compounds of the formula I can be applied to the area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

Surfactants shall be understood as meaning here surface-active compounds which are usually dissolved or dispersed in a liquid and are preferably adsorbed at interfaces. A surfactant molecule contains at least one group having affinity for substances of strong polarity—thereby generally causing solubility in water—and at least one further group having weak affinity for water. Surfactants are therefore molecules containing a hydrophobic (i.e. lipophilic) component, usually a hydrocarbon radical containing alkyl or aryl moieties, and a hydrophilic (i.e. lipophobic) component, e.g. a perfluoroalkyl radical. The products used in actual practice are usually mixtures of these compounds. Surfactants permit not only a dispersion of the active ingredient in a liquid, e.g. aqueous, medium, but also an increased wettability of the plants, which results in a reduction of the amount of active ingredient in the ready-for-use composition and consequently in a lesser environmental impact.

The content of active ingredient in commercial compositions is from 0.01% to 90% by weight and that of adjuvants is 10 to 99.99% by weight, these latter generally comprising 0 to 30% by weight of a surfactant.

The invention also relates to compositions which contain a compound of the formula I as at least one active ingredient, and to the use of such compositions for regulating plant growth and/or for controlling and/or preventing attack by microorganisms. In addition, the invention also relates to the preparation of said compositions, which comprises homogeneously mixing the active ingredient with one or more substances or groups of substances as described herein. The invention further relates to a method of treating plants, which comprises applying thereto the compounds of the formula I or compositions containing them.

The invention is illustrated in more detail by the following Examples, in which percentages are by weight. Unless specifically stated to the contrary, reference to a compound of the formula I will always mean the mixture of racemates or diastereomers. If there is no selective synthesis of pure isomers, then a compound of the formula I is always obtained as a mixture of all possible isomers.

PREPARATORY EXAMPLES

EXAMPLE 1

(a) Preparation of a starting material

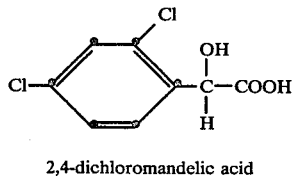

(VII)

2,4-dichloromandelic acid 51.6 g (0.2 mole) of 2,4,1′,1′-tetrachloroacetophenone are added dropwise at 60° C. over 30 minutes to a solution of 29.4 g of sodium hydroxide in 300 ml of water, while keeping the reaction temperature at 60° C. by controlling the rate of addition. The mixture is subsequently stirred for 1 hour, filtered, and then 37% hydrochloric acid is added. After repeated extraction with diethyl ether, the combined extracts are washed with water and dried over sodium sulfate, then filtered and evaporated to dryness, affording colourless crystals with a melting point of 107°–111° C.

(b) Preparation of the intermediate

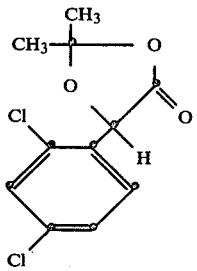

(VIII)

2,2-dimethyl-4-(2,4-dichlorophenyl)-1,3-dioxolan-5-one

A solution of 221 g (1 mole) of 2,4-dichloromandelic acid and 450 ml of acetone is cooled to −10° to −20° C. and then 100 g (54.3 ml) of 98% sulfuric acid are added dropwise. The mixture is then stirred for 2 hours at −20° C. The reaction mixture is then poured into a solution of 200 g of sodium carbonate in 1.8 liters of water and the precipitate is collected by filtration, washed with water and dissolved in methylene chloride. The methylene chloride solution is dried over sodium sulfate and the solvent is removed, yielding the title compound with a melting point of 57°–58° C.

(c) Preparation of the intermediate

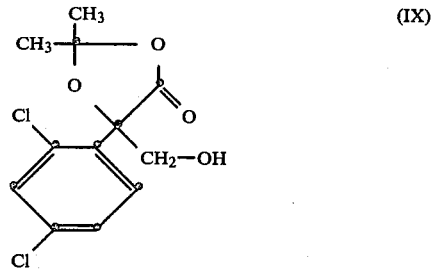

(IX)

2,2-dimethyl-4-(2,4-dichlorophenyl)-4-hydroxymethyl-1,3-dioxolan-5-one 104.4 g (0.4 mole) of 2,2-dimethyl-4-(2,4-dichlorophenyl)-1,3-dioxolan-5-one are dissolved in 700 ml of pyridine and to the solution are added 48 g of paraformaldehyde. Then 40 ml of a 40% solution of tetramethylammonium hydroxide in methanol are slowly added dropwise. The mixture is stirred for 12 hours, cooled to −5° C., and a solution of 100 ml of glacial acetic acid and 400 ml of pyridine is added dropwise until the pH value is 6.5 to 7. The reaction solution is poured into ice-water and extracted with methylene chloride. The extract is dried over sodium sulfate and the product is crystallised by addition of diethyl ether. The crystalline precipitate is washed with a small amount of diethyl ether and petroleum ether. It has a melting point of 182°–185° C.

(d) Preparation of the intermediate

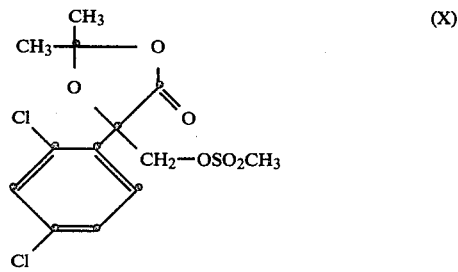

(X)

2,2-dimethyl-4-(2,4-dichlorophenyl)-4-methanesulfonyloxymethyl-1,3-dioxolan-5-one 63.5 g (0.22 mole) of 2,2-dimethyl-4-(2,4-dichlorophenyl)-4-hydroxymethyl-1,3-dioxolan-5-one are dissolved in 400 ml of pyridine and to this solution are added 28.9 g of methanesulfonyl chloride at 0° to 5° C. The resultant suspension is stirred for 2 hours at the same temperature, then poured into ice-water and extracted with methylene chloride. The extract is washed with water, dried over sodium sulfate and evaporated to dryness. The residual resin is crystallised by addition of a small amount of diethyl ether/hexane and the product is isolated by filtration. Melting point: 98°–100° C.

(e) Preparation of the final product

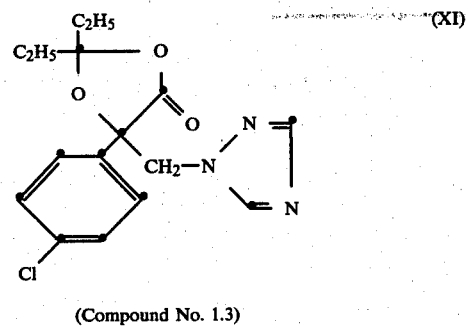

(Compound No. 1.3)

4-(1H-1,2,4-triazolylmethyl)-4-(4-chlorophenyl)-2,2-diethyl-1,3-dioxolan-5-one

With stirring and under nitrogen 5.2 g of sodium hydride (55% dispersion in oil) are added to 50 ml of absolute dimethyl formamide and then 16.6 g of 1,2,4-triazole are added dropwise, whereupon elemental hydrogen escapes. The reaction mixture is heated for 2 hours to 70° C., then cooled to room temperature and a solution of 29 g (0.08 mole) of 2,2-diethyl-4-(chlorophenyl)-4-methanesulfonyloxymethyl-1,3-dioxolan-5-one in 50 ml of dimethyl formamide are added dropwise. The mixture is then heated until the reaction is complete. The reaction solution is cooled and, after addition of 100 ml of ice-water, the mixture is poured into ice-water. The precipitate is isolated by filtration and dissolved in methylene chloride. The methylene chloride solution is washed with water and dried over sodium sulfate and evaporated to dryness to form a resin, which crystallises by addition of a small amount of diethyl ether. The crystals are collected by filtration and washed with petroleum ether. Compound IX has a melting point of 105°–108° C.

The following final products of the formula I as well as intermediates of the respective formula are prepared in analogous manner:

TABLE 1
(Final products)

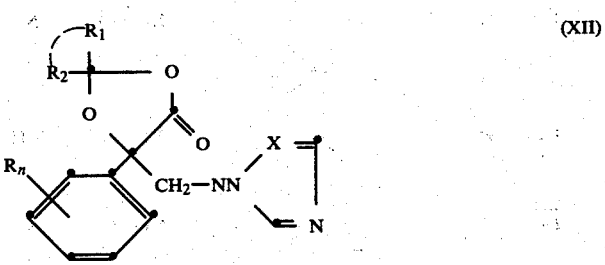

(XII)

| Compound | $R_1$ | $R_2$ | $R_n$ | X | Physical data (°C.) |
|---|---|---|---|---|---|
| 1.1 | $CH_3$ | $CH_3$ | H | N | m.p. 115–116° |
| 1.2 | $CH_3$ | $CH_3$ | 2,4-di-Cl | N | m.p. 153–155° |
| 1.3 | $C_2H_5$ | $C_2H_5$ | 4-Cl | N | m.p. 105–108° |
| 1.4 | $C_2H_5$ | $C_2H_5$ | 4-Cl | CH | m.p. 84–88° |
| 1.5 | $CH_3$ | $CH_3$ | 4-Br | N | m.p. 125–128° |
| 1.6 | $CH_3$ | $C_4H_9$—n | 2,4-di-Cl | N | m.p. 78–85° |
| 1.7 | $CH_3$ | $C_2H_5$ | 2,4-di-Cl | N | m.p. 138–142° |
| 1.8 | $CH_3$ | $C_3H_7$—i | 2,4-di-Cl | N | m.p. 68–71° |
| 1.9 | $C_2H_5$ | $C_2H_5$ | 2,4-di-Cl | N | m.p. 126–128° |
| 1.10 | $CH_3$ | $C_5H_{11}$—n | 2,4-di-Cl | N | |
| 1.11 | $C_5H_{11}$—n | $C_5H_{11}$—n | 2,4-di-Cl | N | |
| 1.12 | $CH_3(CH_2)_8$— | $CH(CH_2)_8$— | 2,4-di-Cl | N | |
| 1.13 | $CH_3$ | $CH_3$ | 2-Cl, 4-F | N | m.p. 144–150° |
| 1.14 | $CH_3(CH_2)_8$— | $CH_3(CH_2)_8$— | 2,4-di-Cl | CH | |
| 1.15 | H | H | 2,4-di-Cl | CH | |
| 1.16 | $C_3H_7(n)$ | $C_3H_7(n)$ | 2,4-di-Cl | N | m.p. 135–139° |
| 1.17 | H | H | H | N | resin |
| 1.18 | H | (cyclopentene) | 2,4-di-Cl | N | |
| 1.19 | H | (cyclopentene) | 2,4-di-Cl | CH | |
| 1.20 | H | Cl-(cyclopentene) | 2,4-di-Cl | N | |
| 1.21 | H | (cyclopentene)-Cl | 2,4-di-Cl | N | |
| 1.22 | H | (cyclopentene)-Cl | 2,4-di-Cl | CH | |

TABLE 1-continued
(Final products)
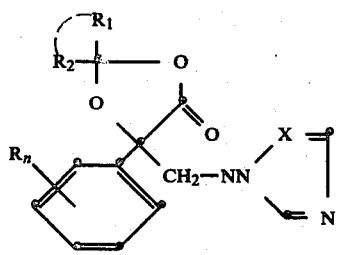
(XII)
| Compound | R₁ | R₂ | Rₙ | X | Physical data (°C.) |
|---|---|---|---|---|---|
| 1.23 | H | —⟨⟩—CH₃ | 2,4-di-Cl | N | |
| 1.24 | H | —⟨⟩—NO₂ | 2,4-di-Cl | N | |
| 1.25 | H | CH₃O—⟨⟩— | 2,4-di-Cl | N | |
| 1.26 | H | —⟨⟩—CH₂ | 2,4-di-Cl | CH | |
| 1.27 | CH₃ | —⟨⟩ | 2,4-di-Cl | N | |
| 1.28 | CH₃ | Cl—⟨⟩—Cl | 2,4-di-Cl | N | |
| 1.29 | CH₃ | —⟨⟩—Cl | 2,4-di-Cl | N | |
| 1.30 | CH₃ | —⟨⟩—CH₃ | 2,4-di-Cl | N | |
| 1.31 | CH₃ | —⟨⟩—NO₂ | 2,4-di-Cl | N | |
| 1.32 | CH₃ | —⟨⟩—Br | 2,4-di-Cl | CH | |
| 1.33 | CH₃ | —CH₂—⟨⟩(Cl,Cl) | 2,4-di-Cl | N | |
| 1.34 | CH₃ | —⟨⟩—Cl | 2,4-di-Cl | CH | |
| 1.35 | H | —⟨⟩ | 4-Cl | N | m.p. 120–122° |
| 1.36 | H | —⟨⟩—Cl | 4-CH₃ | N | |

TABLE 1-continued
(Final products)
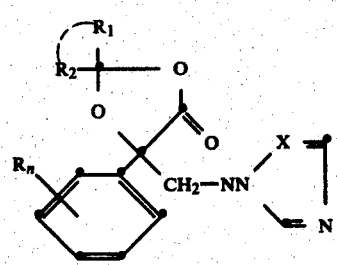
(XII)
| Compound | R₁ | R₂ | Rₙ | X | Physical data (°C.) |
|---|---|---|---|---|---|
| 1.37 | H | (furyl) | 2,5-di-CH₃ | N | |
| 1.38 | CH₃ | CH₃ | 4-Cl | N | |
| 1.39 | H | (furyl-NO₂) | 2-F | CH | |
| 1.40 | H | (furyl-Cl) | 4-OCH₃ | N | |
| 1.41 | H | H | 2,5-di-CH₃ | N | |
| 1.42 | H | H | 2,5-di-CH₃ | CH | |
| 1.43 | CH₃ | C₅H₁₁—n | 2,5-di-CH₃ | N | |
| 1.44 | CH₃ | —CH(CH₃)₂ | 4-Cl | N | |
| 1.45 | H | (furyl-Cl) | 4-Cl | N | |
| 1.46 | CH₃ | (furyl-di-Cl) | 4-Cl | N | |
| 1.47 | C₂H₅ | (furyl) | 4-Cl | N | |
| 1.48 | H | CCl₃ | 4-Cl | N | |
| 1.49 | H | CBr₃ | 2,4-di-Cl | N | |
| 1.50 | (furyl) | (furyl) | 2,4-di-Cl | N | |
| 1.51 | CH₃ | —CH₂-(furyl) | 2,4-di-Cl | N | |
| 1.52 | CH₃ | (furyl-CF₃) | 2,4-di-Cl | N | |
| 1.53 | CH₃ | CH₃ | 4-NO₂ | N | |
| 1.54 | H | —CH₂-(furyl) | 2,4-di-Cl | N | |
| 1.55 | H | C₃H₇—n | 2,4-di-Cl | N | |

TABLE 1-continued
(Final products)

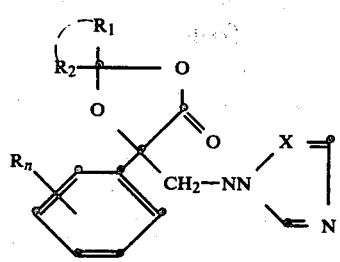
(XII)

| Compound | R₁ | R₂ | Rₙ | X | Physical data (°C.) |
|---|---|---|---|---|---|
| 1.56 | H | -C(CH₃)₃ | 2,4-di-Cl | N | |
| 1.57 | CH₃ | -CH₂-O-Ph | 2,4-di-Cl | N | |
| 1.58 | CH₃ | -CH₂-O-Ph | 2,4-di-Cl | CH | |
| 1.59 | CH₃ | -CH₂-O-CH₃ | 2,4-di-Cl | N | |
| 1.60 | CH₃ | -CH₂-O-CH₃ | 4-Cl | CH | |
| 1.61 | CH₃ | CH₃ | 2-OCH₃ | N | |
| 1.62 | CH₃ | CH₃ | 4-OCH₃ | N | |
| 1.63 | CH₃ | CH₃ | 2-OCH₃ | CH | |
| 1.64 | C₂H₅ | C₂H₅ | 2-OCH₃ | N | |
| 1.65 | CH₃ | CH₃ | 2,4-di-OCH₃ | N | |
| 1.66 | CH₃ | CH₃ | 2-OC₂H₅ | N | |
| 1.67 | H | H | 2-OCH₃ | CH | |
| 1.68 | H | H | 2-OC₃H₇-i | N | |
| 1.69 | CH₃ | CH₃ | 2-OC₃H₇-i | N | |
| 1.70 | C₂H₅ | C₂H₅ | 4-OC₃H₇-i | N | |

TABLE 1a
(Final products)

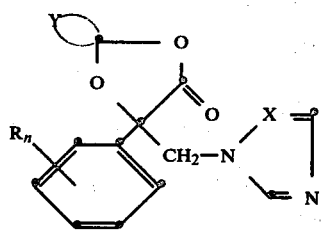
(XIII)

| Compound | Rₙ | Y | X | Physical data (°C.) |
|---|---|---|---|---|
| 1.71 | 2,4-di-Cl | (cyclohexyl) | N | m.p. 132–135° |
| 1.72 | 2,4-di-Cl | (cyclopentyl) | N | |
| 1.73 | 2,4-di-Cl | (cyclobutyl) | N | |
| 1.74 | 2,4-di-Cl | (cyclopropyl) | N | |

TABLE 1a-continued
(Final products)

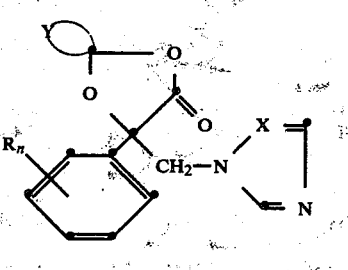
(XIII)

| Compound | Rₙ | Y | X | Physical data (°C.) |
|---|---|---|---|---|
| 1.75 | 2,4-di-Cl | (cyclohexyl) | CH | |
| 1.76 | 4-Cl | (cyclohexyl) | N | |
| 1.77 | 2,5-Di-Cl | (cyclohexyl) | N | |
| 1.78 | 4-Br | (cyclohexyl) | N | m.p. 137–138° |

TABLE 2
(Intermediates)

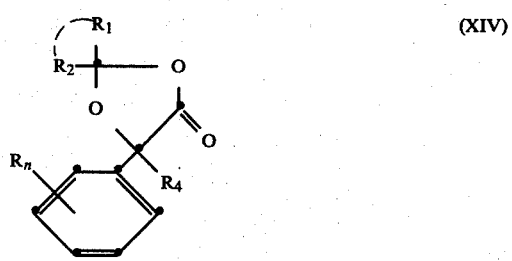
(XIV)

| Compound | $R_1$ | $R_2$ | $R_n$ | $R_4$ | Physical data (°C.) |
|---|---|---|---|---|---|
| 2.1 | $CH_3$ | $CH_3$ | H | H | m.p. 42–43° |
| 2.2 | $CH_3$ | $CH_3$ | H | $CH_2OH$ | viscous oil |
| 2.3 | $CH_3$ | $CH_3$ | H | $CH_2OSO_2CH_3$ | m.p. 65–71° |
| 2.4 | $CH_3$ | $CH_3$ | 2,4-Di-Cl | H | m.p. 57–58° |
| 2.5 | $CH_3$ | $CH_3$ | 2,4-Di-Cl | $CH_2OH$ | m.p. 181–182° |
| 2.6 | $CH_3$ | $CH_3$ | 2,4-di-Cl | $CH_2OSO_2CH_3$ | m.p. 95–100° |
| 2.7 | $C_2H_5$ | $C_2H_5$ | 4-Cl | H | b.p. 130–132°/0.7 torr |
| 2.8 | $C_2H_5$ | $C_2H_5$ | 4-Cl | $CH_2OH$ | m.p. 83–84° |
| 2.9 | $C_2H_5$ | $C_2H_5$ | 4-Cl | $CH_2OSO_2CH_3$ | m.p. 60–63° |
| 2.10 | $CH_3$ | $C_4H_9-n$ | 2,4-di-Cl | H | viscous oil |
| 2.11 | $CH_3$ | $C_4H_9-n$ | 2,4-di-Cl | $CH_2OH$ | resin |
| 2.12 | $CH_3$ | $C_4H_9-n$ | 2,4-di-Cl | $CH_2OSO_2CH_3$ | resin |
| 2.13 | $C_3H_7-n$ | $C_3H_7-n$ | 2,4-di-Cl | H | m.p. 41–43° |
| 2.14 | $C_3H_7-n$ | $C_3H_7-n$ | 2,4-di-Cl | $CH_2OH$ | resin |
| 2.15 | $C_3H_7-n$ | $C_3H_7-n$ | 2,4-di-Cl | $CH_2OSO_2CH_3$ | m.p. 49–51° |
| 2.16 | $C_2H_5$ | $C_2H_5$ | 2,4-di-Cl | H | b.p. 146–148°/0.8 torr |
| 2.17 | $C_2H_5$ | $C_2H_5$ | 2,4-di-Cl | $CH_2OH$ | m.p. 129–132° |
| 2.18 | $C_2H_5$ | $C_2H_5$ | 2,4-di-Cl | $CH_2OSO_2CH_3$ | m.p. 75–77° |
| 2.19 | H | $CCl_3$ | 2,4-di-Cl | H | m.p. 90–94° |
| 2.20 | $CH_3$ | $CH_3$ | 4-Br | H | m.p. 62–64° |
| 2.21 | $CH_3$ | $CH_3$ | 4-Br | $CH_2OH$ | m.p. 123–127° |
| 2.22 | $CH_3$ | $CH_3$ | 4-Br | $CH_2OSO_2CH_3$ | m.p. 73–76° |
| 2.23 | $CH_3$ | $CH_3$ | 4-Br | $CH_2O-$Tosyl | m.p. 67–70° |
| 2.24 | $CH_3$ | $C_3H_7-i$ | 2,4-di-Cl | H | resin |
| 2.25 | $CH_3$ | $C_3H_7-i$ | 2,4-di-Cl | $CH_2OH$ | resin |
| 2.26 | $CH_3$ | $C_3H_7-i$ | 2,4-di-Cl | $CH_2OSO_2CH_3$ | resin |
| 2.27 | H | $C_6H_5$ | 4-Cl | H | m.p. 78–81° |
| 2.28 | H | $C_6H_5$ | 4-Cl | $CH_2OH$ | resin |
| 2.29 | H | $C_6H_5$ | 4-Cl | $CH_2OSO_2CH_3$ | resin |
| 2.30 | $CH_3$ | $CH_3$ | 2,4-di-Cl | H | m.p. 61–63° |
| 2.31 | H | H | H | H | oil |
| 2.32 | H | H | H | $CH_2OH$ | resin |
| 2.33 | H | H | H | $CH_2OSO_2CH_3$ | resin |
| 2.34 | $-(CH_2)_5-$ | | 2,4-di-Cl | H | m.p. 60–66° |
| 2.35 | $-(CH_2)_5-$ | | 2,4-di-Cl | $CH_2OH$ | resin |
| 2.36 | $-(CH_2)_5-$ | | 2,4-di-Cl | $CH_2OSO_2CH_3$ | resin |
| 2.37 | $-(CH_2)_5-$ | | 4-Br | H | m.p. 79–81° |
| 2.38 | $-(CH_2)_5-$ | | 4-Br | $CH_2OH$ | resin |
| 2.39 | $-(CH_2)_5-$ | | 4-Br | $CH_2OSO_2CH_3$ | m.p. 65–68° |
| 2.40 | $-(CH_2)_4-$ | | 2,4-di-Cl | H | m.p. 59–61° |
| 2.41 | $-(CH_2)_4-$ | | 2,4-di-Cl | $CH_2OH$ | resin |
| 2.42 | $-(CH_2)_4-$ | | 2,4-di-Cl | $CH_2OSO_2CH_3$ | resin |

For application, the compounds of the formula I can be processed to the following formulations:

FORMULATION EXAMPLES

EXAMPLE 2

Solid formulations:

Dusts and tracking powders contain in general up to 10% of active ingredient. A 5% dust can consist for example of 5 parts of active ingredient and 95 parts of an adjuvant, such as talcum, or of 5 parts of active ingredient, 3 parts of highly dispersed silica and 92 parts of talcum. Further mixtures with these and other carriers and adjuvants commonly employed in the art of formulation are also possible. These dusts are produced by mixing and grinding the active ingredients with the carriers and adjuvants, and can be applied in this form by dusting.

Granulates, such as coating, impregnated and homogeneous granulates and also pellets, usually contain 1 to 80% of active ingredient. A 5% granulate can thus be composed of e.g. 5 parts of active ingredient, 0.25 part of epoxidised vegetable oil, 0.25 part of cetyl polyglycol ether, 3.50 parts of polyethylene glycol and 91 parts of kaolin (preferred particle size 0.3–0.8 mm). The granulate can be prepared as follows: The active ingredient is mixed with the vegetable oil, the mixture is dissolved in 6 parts of acetone, and the polyethylene glycol and cetyl polyglycol ether are added. The solution obtained is sprayed onto kaolin, and the acetone is subsequently evaporated off in vacuo. A microgranulate of this type is advantageously used for controlling soil fungi.

EXAMPLE 3

Liquid formulations:

A distinction is generally made between active ingredient concentrates which are dispersible or soluble in water, and aerosols. Active ingredient concentrates dispersible in water include e.g. wettable powders and pastes, which usually contain 25-90% of active ingredient in commercial packs, and 0.01 to 15% of active ingredient in ready-for-use solutions. Emulsifiable concentrates contain 10 to 50% of active ingredient, and solution concentrates contain in ready-for-use solution 0.0001 to 20% of active ingredient. A 70% wettable powder can thus be composed of e.g. 70 parts of active ingredient, 5 parts of sodium dibutylnaphthalene sulfonate, 3 parts of naphthalenesulfonic acid/phenolsulfonic acid/formaldehyde condensate (in the ratio of 3:2:1), 10 parts of kaolin and 12 parts of chalk, for example Champagne chalk. A 40% wettable powder can consist e.g. of the following substances: 40 parts of active ingredient, 5 parts of sodium lignosulfonate, 1 part of sodium dibutylnaphthalenesulfonate and 54 parts of silicic acid. A 25% wettable powder can be formulated in different ways. It can be composed e.g. of: 25 parts of active ingredient, 4.5 parts of calcium lignosulfonate, 1.9 parts of chalk, for example a mixture of Champagne chalk/hydroxyethylene cellulose (1:1), 1.5 parts of sodium dibutylnaphthalenesulfonate, 19.5 parts of silicic acid, 19.5 parts of Champagne chalk and 28.1 parts of kaolin. A 25% wettable powder can also consist of e.g.: 25 parts of active ingredient, 2.5 parts of isooctylphenoxypolyoxyethylene-ethanol, 1.7 parts of a mixture of Champagne chalk/hydroxyethyl cellulose (1:1), 8.3 parts of sodium silicate, 16.5 parts of kieselguhr and 46 parts of kaolin. A 10% wettable powder can be formulated e.g. from: 10 parts of active ingredient, 3 parts of a mixture of the sodium salts of saturated fatty alcohol sulfonates, 5 parts of naphthalenesulfonic acid/formaldehyde condensate and 82 parts of kaolin. Other wettable powders can be formulated as mixtures of 5 to 30% of active ingredient together with 5 parts of an absorbent carrier material, such as silicic acid, 55 to 80 parts of a carrier such as kaolin, and a dispersing agent mixture consisting of 5 parts of sodium arylsulfonate and 5 parts of an alkylaryl polyglycol ether. A 25% emulsifiable concentrate can contain e.g. the following emulsifiable substances: 25 parts of active ingredient, 2.5 parts of epoxidised vegetable oil, 10 parts of a mixture of an alkylarylsulfonate and a fatty alcohol polyglycol ether, 5 parts of dimethyl formamide and 57.5 parts of xylene. Emulsions of the desired concentration can be prepared from such concentrates by dilution with water. These emulsions are particularly suitable for leaf application. It is, moreover, possible to produce further wettable powders having other mixture ratios and containing other carriers and adjuvants customarily employed in formulation technology. The active ingredients are intimately mixed in suitable mixers with the stated adjuvants, and subsequently ground on the appropriate mills and rollers. Wettable powders having excellent wetting and suspension properties are obtained. These wettable powders can be diluted with water to obtain suspensions of the desired concentration, and are particularly suitable for leaf application. The invention also relates to such compositions.

Compositions formulated as described above and containing a compound of the formula I as active ingredient (e.g. compounds 1.1 to 1.9, 1.13, 1.16, 1.35, 1.38, 1.71 or 1.78) can be used very successfully for regulating plant growth and/or for controlling phytopathogenic microorganisms. Other compounds of Tables 1 and 1a can also be used with equally good or similar success.

BIOLOGICAL EXAMPLES

The spray mixtures used in the following Examples were formulated as described above.

EXAMPLE 4

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 0.5 and 2.5 kg respectively of active ingredient per hectare. Evaluation of the growth of the cereals is made 10 and 21 days after application. Compared with untreated controls, the growth of cereal plants treated with compounds of the formula I is greatly reduced. Particularly effective compounds of the formula I are those in which the substituent A is an unsubstituted or a halogen-substituted phenyl radical. They include compounds 1.1 to 1.9, 1.38, 1.71 and 2.9.

EXAMPLE 5

Growth inhibition of grasses

Seeds of the grasses Lolium perenne, Poa pratensis, Festuca ovina, and Cynodon dactylon are sown in plastic dishes filled with an earth/peat/sand mixture (6:3:1), in a greenhouse, and watered as required. The emergent grasses are cut back weekly to a height of 4 cm above the soil and, 50 days after sowing and 1 day after the last cut, are sprayed with an aqueous spray mixture of an active ingredient of the formula I. The concentration of active ingredient corresponds to a rate of application of 2.5 kg per hectare. The growth of the grasses is evaluated 10 and 21 days after application. The compounds of Tables 1 and 1a effect a marked reduction in growth, especially compounds 1.1 to 1.9, 1.38, 1.71 and 2.9.

EXAMPLE 6

Increase in crop yield by regulating the growth of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. Evaluation is made about 5 weeks after application. Compared with untreated controls, the compounds of the formula I markedly increase the number and weight of the harvested siliques. Compounds 1.1 to 1.9, 1.38, 1.71 and 2.9 are particularly effective.

EXAMPLE 7

Action against Erysiphe graminis on barley (a) Residual protective action

Barley plants about 8 cm in height are sprayed with a spray mixture (0.02% of active ingredient) prepared from the active ingredient formulated as a wettable powder. The treated plants are dusted with conidia of the fungus after 3-4 hours. The infected barley plants are then stood in a greenhouse at about 22° C. The extent of the infestation is evaluated after 10 days.

(b) Systemic action

Barley plants about 8 cm in height are treated with a spray mixture (0.006% of active ingredient, based on the volume of the soil) prepared from the active ingredient formulated as wettable powder. Care is taken that the spray mixture does not come in contact with the parts of the plants above the soil. The treaated plants are infected 48 hours later with a conidia suspension of the fungus. The infected barley plants are then stood in a greenhouse at about 22° C. and evaluation of infestation is made after 10 days.

In residual-protective treatment of barley plants against Erysiphe fungi with compounds of the formula I, e.g. compounds 1.1, 1.2, 1.3, 1.4, 1.5, 1.6, 1.7, 1.8, 1.13, 1.16, 1.38 or 1.71, attack is reduced to less than 10% compared with controls (100% attack). In addition, compounds 1.1, 1.2, 1.3, 1.4, 1.13, 1.38, 1.5, 1.6 and 1.8 have a very good systemic action. Intermediates of the formula V and, in particular, of the formula VI (G=O-SO$_2$CH$_3$) exhibit fungicidal action in this test.

Groundnut plants 10-15 cm in height are sprayed with a wettable powder containing 0.02% of active ingredient and infected 48 hours later with a conidia suspension of the fungus. The infected plants are incubated for 72 hours at about 21° C. and high humidity and then put into a greenhouse until the typical leaf specks occur. Evaluation of the fungicidal action is made 12 days after infection, and is based on the number and size of the specks. Compared with untreated controls (number and size of the specks=100%), the plants treated with compounds of the formula I exhibit insignificant or almost no attack by fungus. Among others, compounds 1.1 to 1.9, 1.13 and 1.38 inhibit speck development almost completely (0 to 5% attack).

EXAMPLE 8

Action against Puccinia graminis on wheat (a) Residual-protective action

Wheat plants treated 6 days after sowing with a spray mixture prepared from a wettable powder formulation of the active ingredient (0.06%). After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection. Among others, compounds 1.1, 1.2, 1.13, 1.3, 1.5, 1.6 and 1.8 have a good residual-protective action. They inhibit rust pustule development almost completely (0 to 5% attack).

(b) Systemic action

Wheat plants are treated 5 days after sowing with a spray mixture prepared from a wettable powder formulation of the active ingredient (0.006%, based on the volume of the soil). After 48 hours the treated plants are infected with a uredospore suspension of the fungus. The plants are then incubated for 48 hours at 95-100% relative humidity and about 20° C. and then stood in a greenhouse at about 22° C. Evaluation of rust pustule development is made 12 days after infection. Among others, compounds 1.1, 1.2, 1.3, 1.13, 1.38, 1.5 and 1.8 inhibited rust pustule development almost completely (0 to 5% attack).

EXAMPLE 9

Residual-protective action against Venturia inaequalis on apple shoots

Apple cuttings with 10-20 cm long fresh shoots are sprayed with a spray mixture prepared from a wettable powder formulation of the active ingredient (0.06%). After 24 hours the treated plants are infected with a conidia suspension of the fungus. The plants are then incubated for 5 days at 90-100% relative humidity and stood in a greenhouse for a further 10 days at 20°-24° C. Scab infestation is evaluated 15 days after infection. Compounds of the formula I are very effective against Venturis pathogens. Compounds 1.1, 1.2, 1.3, 1.13, 1.38, 1.4, 1.5 and 1.6 in particular inhibit scab infestation to less than 20% compared with untreated controls. Compounds 1.3, 1.4, 1.13, 1.38 and 1.5 do so even in a concentration of 0.02%.

What is claimed is:

1. A compound of the formula I

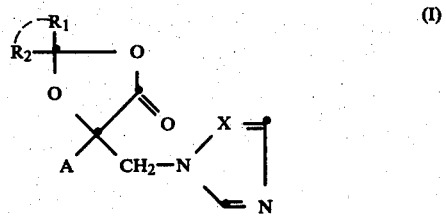

wherein each of R$_1$ and R$_2$ independently is hydrogen, C$_1$-C$_8$alkyl, unsubstituted or mono- or polysubstituted by halogen, C$_1$-C$_4$alkoxy, C$_1$-C$_4$alkylthio, phenyl or phenoxy, or is phenyl, all of which phenyl radicals are unsubstituted or mono- or polysubstituted by halogen, nitro, trifluoromethyl, C$_1$-C$_4$alkyl or methoxy, or R$_1$ and R$_2$ together form a 3- to 7-membered cycloalkyl ring which is unsubstituted or substituted by halogen, C$_1$-C$_4$alkyl, C$_1$-C$_4$alkoxy or C$_1$-C$_3$alkylthio, A is a phenyl radical unsubstituted or mono- or polysubstituted by halogen, trifluoromethyl, nitro, C$_1$-C$_4$alkyl, C$_1$-C$_4$alkoxy or phenyl, and X is —CH= or —N=, or an acid addition salt thereof with organic or inorganic acids, or a metal complex salt thereof.

2. A compound according to claim 1, wherein each of R$_1$ and R$_2$ independently is hydrogen, C$_1$-C$_8$alkyl, phenyl which is unsubstituted or substituted by halogen, nitro, trifluoromethyl, methyl or ethyl, or is benzyl.

3. A compound according to claim 2, wherein each of R$_1$ and R$_2$ independently is hydrogen, C$_1$-C$_5$alkyl or phenyl, and A is phenyl, unsubstituted or mono- or polysubstituted by halogen, C$_1$-C$_3$alkyl, methoxy or phenyl.

4. A compound according to claim 3, wherein each of R$_1$ and R$_2$ independently is C$_1$-C$_5$alkyl, and A is phenyl, 2,4-dichlorophenyl, 2,4-dibromophenyl, 4-chlorophenyl, 2-chloro-4-fluorophenyl or 4-bromophenyl.

5. A compound according to claim 1, wherein R$_1$ and R$_2$ together form a 3- to 7-membered cycloalkyl ring which is unsubstituted or substituted by methoxy.

6. A 1,2,4-triazolyl derivative of the formula I according to claim 1.

7. A compound according to claim 1, selected from the group consisting of 4-(1H-1,2,4-triazolylmethyl)-4-(4-chlorophenyl)-2,2-dimethyl-1,3-dioxolan-5-one, 4-(1H-1,2,4-triazolylmethyl)-4-(4-bromophenyl)-2,2-dimethyl-1,3-dioxolan-5-one, 4-(1H-1,2,4-triazolylmethyl)-4-(phenyl)-2,2-dimethyl-1,3-dioxolan-5-one, 4-(1H-1,2,4-triazolylmethyl)-4-(2,4-dichlorophenyl)-2,2-dimethyl-1,3-dioxolan-5-one, 4-(1H-imidazolylmethyl)-4-(4-chlorophenyl)-2,2-dimethyl-1,3-dioxolan-5-one, 4-(1H-1,2,4-triazolylmethyl)-4-(4-chlorophenyl)-2,2-diethyl-1,3-dioxolan-5-one, or 4-(1H-1,2,4-triazolylmethyl)-5-(2-chloro-4-fluorophenyl)-2,2-dimethyl-1,3-dioxolan-5-one.

8. A composition for regulating plant growth and/or for controlling and/or preventing attack by microorganisms, said composition containing a compound according to claim 1 as at least one active component and a carrier.

9. A composition according to claim 8 which contains 0.01 to 90% by weight of the compound and 99.99 to 10% by weight of adjuvants, which latter include 0 to 30% by weight of a surfactant.

10. A method of regulating plant growth, which method comprises applying to said plants or to the locus thereof a herbicidally effective amount of a compound according to claims 1 or 7.

11. The method of claim 10 for inhibiting the growth of cereals or grasses.

12. The method of claim 10 for increasing the yield of cereal, soybean, sugar beet, maize or rice crops.

13. The method of claim 10 for increasing the breaking strength of wheat, rye, barley, oats or rice.

14. A method of controlling and/or protecting cultivated plants from attack by phytopathogenic fungi, which method comprises applying to said plants or to the locus thereof a fungicidally effective amount of a compound according to claims 1 or 7.

15. The compound according to claim 7 which is 4-(1H-1,2,4-triazolylmethyl)-4-(4-bromophenyl)-2,2-dimethyl-1,3-dioxolan-5-one.

16. The compound according to claim 4 which is 4-(1H-imidazolylmethyl)-4-(4-chlorophenyl)-2,2-diethyl-1,3-dioxolan-5-one.

* * * * *